United States Patent
Chung et al.

(10) Patent No.: US 9,976,893 B2
(45) Date of Patent: May 22, 2018

(54) METHOD FOR MEASURING PERMITTIVITY OF MATERIAL

(71) Applicant: FINETEK Co., Ltd., New Taipei (TW)

(72) Inventors: Shyh-Jong Chung, New Taipei (TW); I-Chu Lin, New Taipei (TW); Liang-Chi Chang, New Taipei (TW); Chao-Kai Cheng, New Taipei (TW); Yi-Liang Hou, New Taipei (TW)

(73) Assignee: FINETEK CO., LTD., New Taipei (TW)

( * ) Notice: Subject to any disclaimer, the term of this patent is extended or adjusted under 35 U.S.C. 154(b) by 343 days.

(21) Appl. No.: 14/855,964

(22) Filed: Sep. 16, 2015

(65) Prior Publication Data

US 2017/0074711 A1 Mar. 16, 2017

(51) Int. Cl.
*G01S 13/08* (2006.01)
*G01F 25/00* (2006.01)
*G01R 27/26* (2006.01)
*G01N 22/00* (2006.01)
*G01F 23/284* (2006.01)

(52) U.S. Cl.
CPC ......... *G01F 25/0061* (2013.01); *G01N 22/00* (2013.01); *G01R 27/26* (2013.01); *G01F 23/284* (2013.01)

(58) Field of Classification Search
CPC .............................. G01F 25/0061; G01F 22/00
USPC .......................................................... 342/124
See application file for complete search history.

(56) References Cited

U.S. PATENT DOCUMENTS

| | | | | |
|---|---|---|---|---|
| 6,545,603 B1* | 4/2003 | Launay | ................ | G01D 5/2405 340/540 |
| 7,525,476 B1* | 4/2009 | Delin | .................... | G01F 23/284 324/600 |
| 2007/0046289 A1* | 3/2007 | Troxler | .................. | G01N 33/42 324/334 |
| 2010/0070208 A1* | 3/2010 | Sai | ........................ | G01F 23/284 702/55 |
| 2012/0299768 A1* | 11/2012 | Griessbaum | ............ | G01S 7/292 342/124 |
| 2013/0110420 A1* | 5/2013 | Griessbaum | ............ | G01F 23/28 702/55 |

(Continued)

OTHER PUBLICATIONS

M. Weiss and R. Knoche!, "A novel method of determining the permittivity of liquids," in IEEE Transactions on Instrumentation and Measurement, vol. 49, No. 3, pp. 488-492, Jun. 2000. (Year: 2000).*

*Primary Examiner* — Marcus E Windrich
(74) *Attorney, Agent, or Firm* — Chun-Ming Shih; HDLS IPR Services

(57) ABSTRACT

A method for measuring a permittivity (ε) of a material (30) includes following steps. A sensing rod (14) of a material level sensor (10) inserts into a tank (20). The material level sensor (10) proceeds with a material level measurement of the material (30) to obtain a first feature value. The material level sensor (10) is vertically moved with a vertical distance (Hair). The material level sensor (10) proceeds with the material level measurement to obtain a second feature value, and subtracts the first feature value by the second feature value to obtain a feature value variation, and calculates the feature value variation to obtain the permittivity (ε) of the material (30).

10 Claims, 6 Drawing Sheets

(56) References Cited

U.S. PATENT DOCUMENTS

2014/0158897 A1* 6/2014 Troxler ............... G01N 23/203
250/390.06

* cited by examiner

METHOD FOR MEASURING PERMITTIVITY OF MATERIAL

BACKGROUND OF THE INVENTION

Field of the Invention

The present invention relates to a method for measuring a permittivity, and especially relates to a method for measuring a permittivity of a material.

Description of the Related Art

Currently, the material level sensor, for example the time domain reflection radar sensor, is used widely for measuring the material level. Therefore, the material level sensor is very important.

However, a lot of factors will impact the accuracy of the material level sensor, for example the permittivity of the material. This is because the permittivity of the material will impact the round-trip time of the measurement signals in the material, so that the accuracy of the material level sensor is impacted.

However, currently after the material level sensor, for example the time domain reflection radar sensor is installed, the permittivity of the material is not measured accurately and conveniently, so that the accuracy of the material level sensor is decreased.

SUMMARY OF THE INVENTION

In order to solve the above-mentioned problems, an object of the present invention is to provide a method for measuring a permittivity of a material.

In order to achieve the object of the present invention mentioned above, the method for measuring the permittivity of the material is applied to a material level sensor, a tank and the material. The material level sensor comprises a material level sensing circuit and a sensing rod. A top-down of the tank comprises a non-filled area and a filled area filled with the material. The method comprises following steps. The sensing rod of the material level sensor inserts into the tank, so that a part of the sensing rod of the material level sensor is in the non-filled area of the tank, and the other part of the sensing rod of the material level sensor is in the filled area of the tank, and the material level sensor is at a first location. After the material level sensor is at the first location, the material level sensor proceeds with a material level measurement of the material to obtain a first feature value. After the first feature value is obtained, the material level sensor is vertically moved with a vertical distance, but the sensing rod of the material level sensor is not completely away from the filled area of the tank, and the material level sensor is at a second location. After the material level sensor is at the second location, the material level sensor proceeds with the material level measurement of the material to obtain a second feature value. The material level sensing circuit subtracts the first feature value by the second feature value to obtain a feature value variation. The material level sensing circuit calculates the feature value variation to obtain the permittivity of the material.

The advantage of the present invention is to measure and calculate the permittivity of the material to improve the accuracy of the material level sensor.

DETAILED DESCRIPTION OF THE INVENTION

Please refer to following detailed description and figures for the technical content of the present invention. The following detailed description and figures are referred for the present invention, but the present invention is not limited to it.

Figure 1:
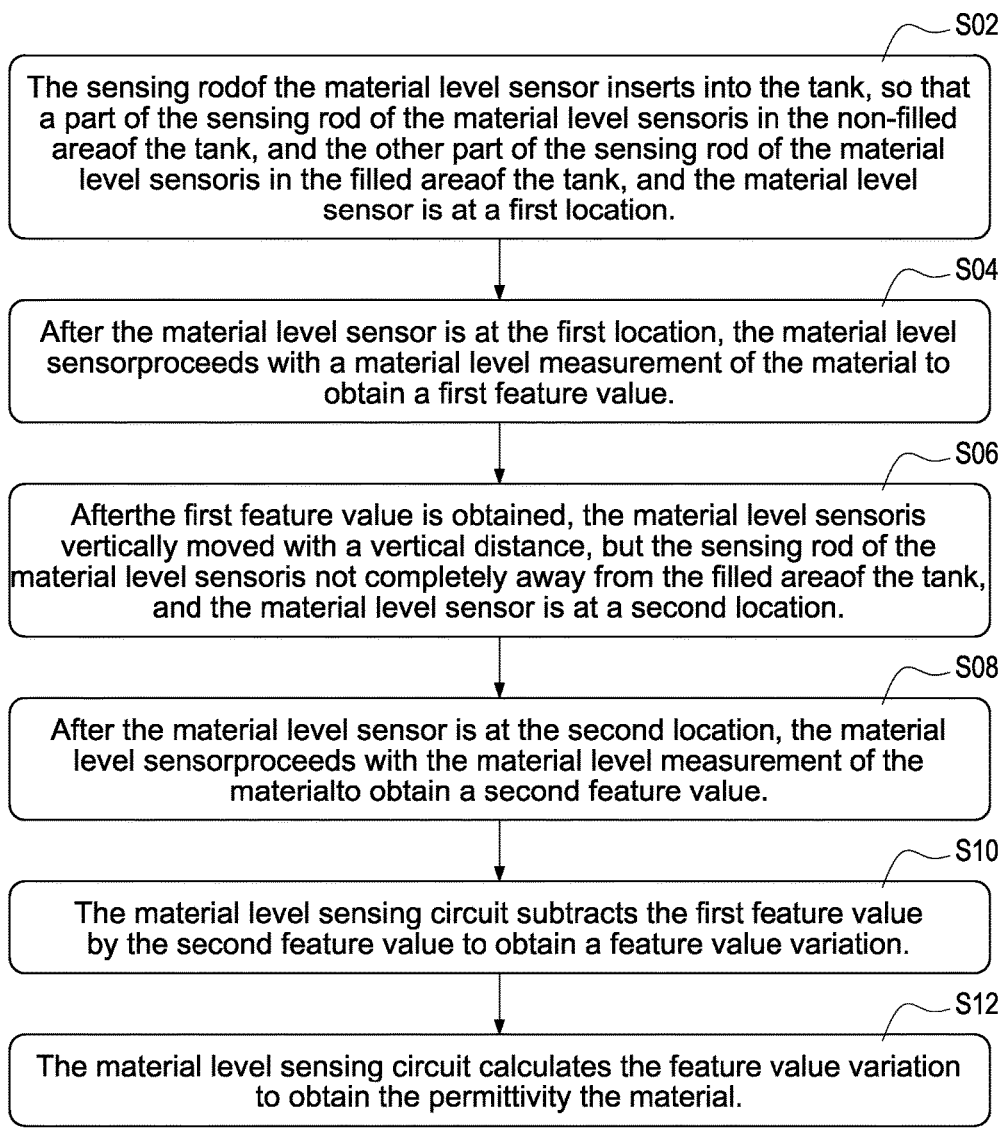
FIG. 1 shows a flow chart of the method for measuring the permittivity of the material of the present invention.
Figure 2A:
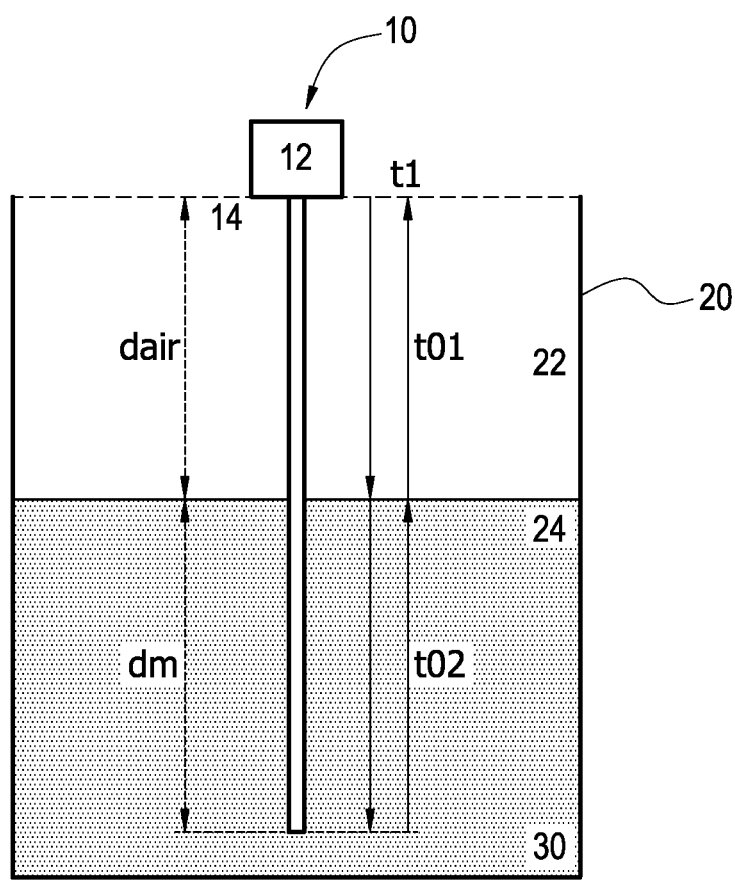
FIG. 2a shows that the material level sensor is at the first location.
Figure 2B:
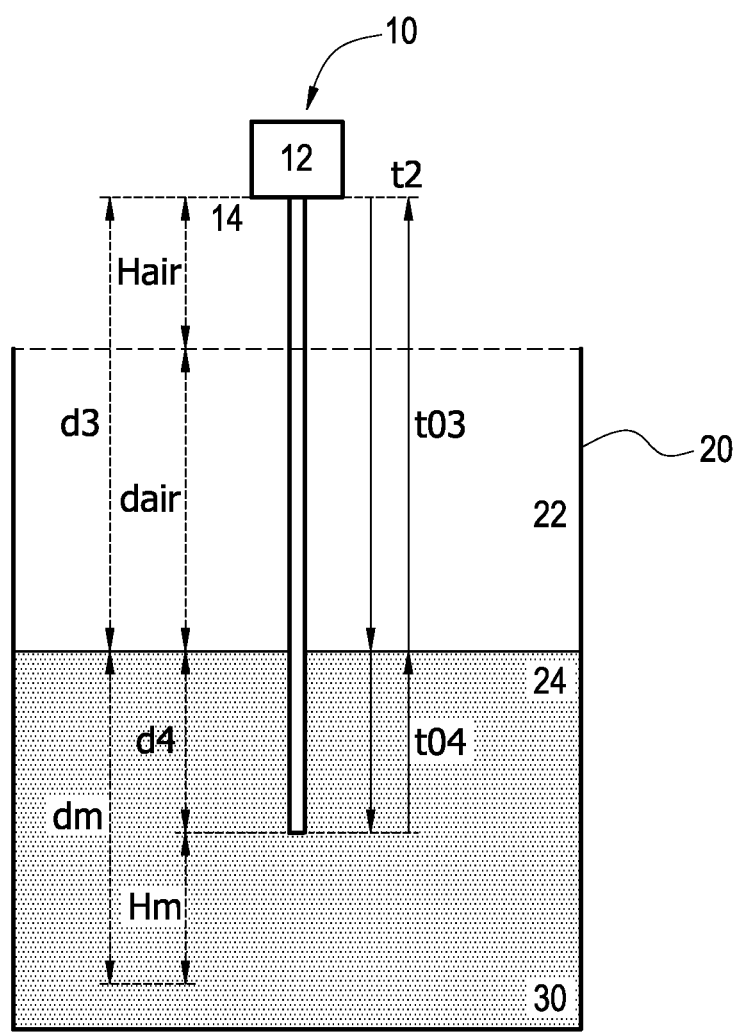
FIG. 2b shows that the material level sensor is at the second location.

FIG. 1 shows a flow chart of the method for measuring the permittivity of the material of the present invention. FIG. 2a shows that the material level sensor is at the first location. FIG. 2b shows that the material level sensor is at the second location.

A method for measuring a permittivity $\varepsilon$ of a material 30 of the present invention is applied to a material level sensor 10, a tank 20 and the material 30. The material level sensor 10 comprises a material level sensing circuit 12 and a sensing rod 14. A top-down of the tank 20 comprises a non-filled area 22 and a filled area 24 filled with the material 30. Namely, from the top to the bottom in the tank 20, there are the non-filled area 22 and the filled area 24 filled with the material 30. The material level sensor 10 is, for example but not limited to, a time domain reflection radar sensor. The method comprises following steps.

First, please refer to FIG. 1 and FIG. 2a.

Step S02: The sensing rod 14 of the material level sensor 10 inserts into the tank 20, so that a part of the sensing rod 14 of the material level sensor 10 is in the non-filled area 22 of the tank 20, and the other part of the sensing rod 14 of the material level sensor 10 is in the filled area 24 of the tank 20, and the material level sensor 10 is at a first location (as shown in FIG. 2a).

Step S04: After the material level sensor 10 is at the first location, the material level sensor 10 proceeds with a material level measurement of the material 30 to obtain a first feature value (will be described in details later).

Step S06: After the first feature value is obtained, the material level sensor 10 is vertically moved with a vertical distance Hair (or a vertical distance Hm), but the sensing rod 14 of the material level sensor 10 is not completely away from the filled area 24 of the tank 20, and the material level sensor 10 is at a second location (as shown in FIG. 2b). Moreover, the vertical distance Hair is equal to the vertical distance Hm.

Step S08: After the material level sensor 10 is at the second location, the material level sensor 10 proceeds with the material level measurement of the material 30 to obtain a second feature value (will be described in details later).

Step S10: The material level sensing circuit 12 subtracts the first feature value by the second feature value to obtain a feature value variation (will be described in details later).

Step S12: The material level sensing circuit 12 calculates the feature value variation to obtain the permittivity $\varepsilon$ of the material 30 (will be described in details later).

The step S02 and the step S04 mentioned above will be described in details as following. Please refer to FIG. 1 and FIG. 2a again.

When the material level sensor 10 is at the first location (as shown in FIG. 2a), a length of the part of the sensing rod 14 of the material level sensor 10 in the non-filled area 22 of the tank 20 is a first length dair, and a length of the other part of the sensing rod 14 of the material level sensor 10 in the filled area 24 of the tank 20 is a second length dm.

The first feature value is a first time-passing difference value t1. The first time-passing difference value t1 is equal to a first time t01 added by a second time t02. The first time t01 is equal to double the first length dair divided by an air-wave velocity Vair. The second time t02 is equal to double the second length dm divided by a material-wave velocity Vm.

The content mentioned above can be shown as following equations:

$$t1=t01+t02=(2*dair/Vair)+(2*dm/Vm)$$

The step S06 and the step S08 mentioned above will be described in details as following. Please refer to FIG. 1 and FIG. 2b again. A third length d3 is equal to the first length dair added by the vertical distance Hair. A fourth length d4 is equal to the second length dm subtracted by the vertical distance Hm (namely, the second length dm is equal to the fourth length d4 added by the vertical distance Hm).

The second feature value is a second time-passing difference value t2. The second time-passing difference value t2 is equal to a third time t03 added by a fourth time t04. The third time t03 is equal to double the third length d3 divided by the air-wave velocity Vair. The fourth time t04 is equal to double the fourth length d4 divided by the material-wave velocity Vm.

The content mentioned above can be shown as following equations:

$$t2=t03+t04=(2*d3/Vair)+(2*d4/Vm)=[2*(dair+Hair)/Vair]+[2*(dm-Hm)/Vm]$$

Moreover, the vertical distance Hair is equal to the vertical distance Hm.

The step S10 mentioned above will be described in details as following. The first feature value (namely, the first time-passing difference value t1) subtracted by the second feature value (namely, the second time-passing difference value t2) is equal to the feature value variation. According to the equations mentioned above, the feature value variation is equal to negative double the vertical distance Hair divided by the air-wave velocity Vair, and then added by double the vertical distance Hm divided by the material-wave velocity Vm.

The content mentioned above can be shown as following equations:

$$\text{The feature value variation}=t1-t2=(-2*Hair/Vair)+(2*Hm/Vm)$$

Figure 3:
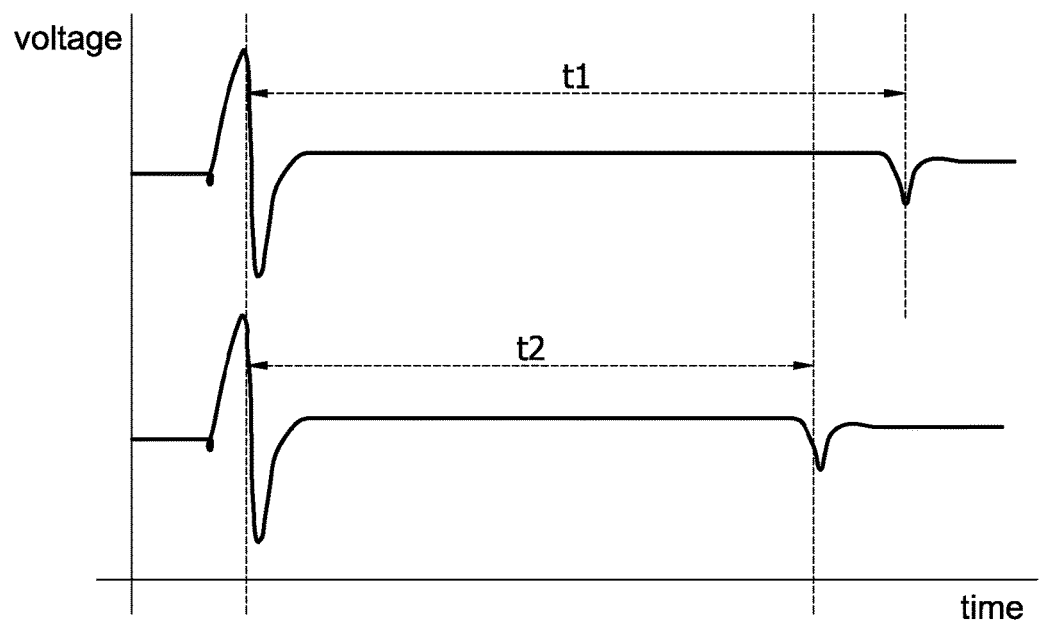
FIG. 3 shows a waveform diagram of an embodiment of the first time-passing difference value and the second time-passing difference value.

FIG. 3 shows a waveform diagram of an embodiment of the first time-passing difference value and the second time-passing difference value. Please refer to FIG. 2a and FIG. 2b. As shown in FIG. 3, in an embodiment, the air-wave velocity Vair is greater than the material-wave velocity Vm, so the second time-passing difference value t2 is less than the first time-passing difference value t1. Namely, the first time-passing difference value t1 is greater than the second time-passing difference value t2.

The step S12 mentioned above will be described in details as following. The feature value variation is calculated to obtain the permittivity ε of the material 30. Moreover, the air-wave velocity Vair is a constant c. A square root of the permittivity ε is a square root value $\sqrt{\varepsilon}$. The material-wave velocity Vm is equal to the constant c divided by the square root value $\sqrt{\varepsilon}$.

The content mentioned above can be shown as following equation:

$$Vm=c/\sqrt{\varepsilon}$$

$$\text{Therefore, the feature value variation}=t1-t2=(-2*Hair/Vair)+(2*Hm/Vm)=(-2*Hair/c)+[2*Hm/(c/\sqrt{\varepsilon})]=(-2*Hair/c)+(\sqrt{\varepsilon}*2*Hm/c)=(-2*Hair/c)+(\sqrt{\varepsilon}*2*Hair/c)=2*Hair*(\sqrt{\varepsilon}-1)/c$$

$$\text{Therefore, the feature value variation}*c/(2*Hair)=\sqrt{\varepsilon}-1$$

$$[\text{the feature value variation}*c/(2*Hair)]+1=\sqrt{\varepsilon}$$

$$\{[\text{the feature value variation}*c/(2*Hair)]+1\}2=\varepsilon$$

As mentioned above, the first feature value (namely, the first time-passing difference value t1) subtracted by the second feature value (namely, the second time-passing difference value t2) is equal to the feature value variation. The first time-passing difference value t1 and the second time-passing difference value t2 can be obtained by the material level sensor 10. Therefore, the feature value variation is obtained. The constant c and the vertical distance Hair are known. Therefore, according to the equations mentioned above, the permittivity ε is obtained.

According to the permittivity ε obtained by the method of the present invention mentioned above, the depth (namely, the level) of the material 30 can be obtained by using the permittivity ε. This will be described in details as following.

Figure 4A:
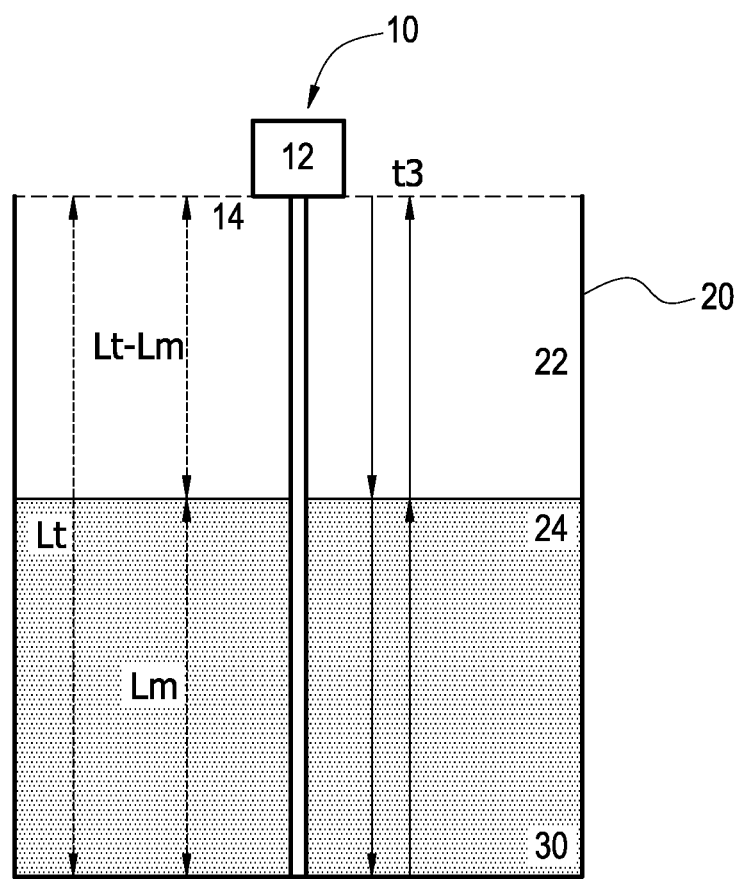
FIG. 4a shows a part of the method for measuring the depth of the material.
Figure 4B:
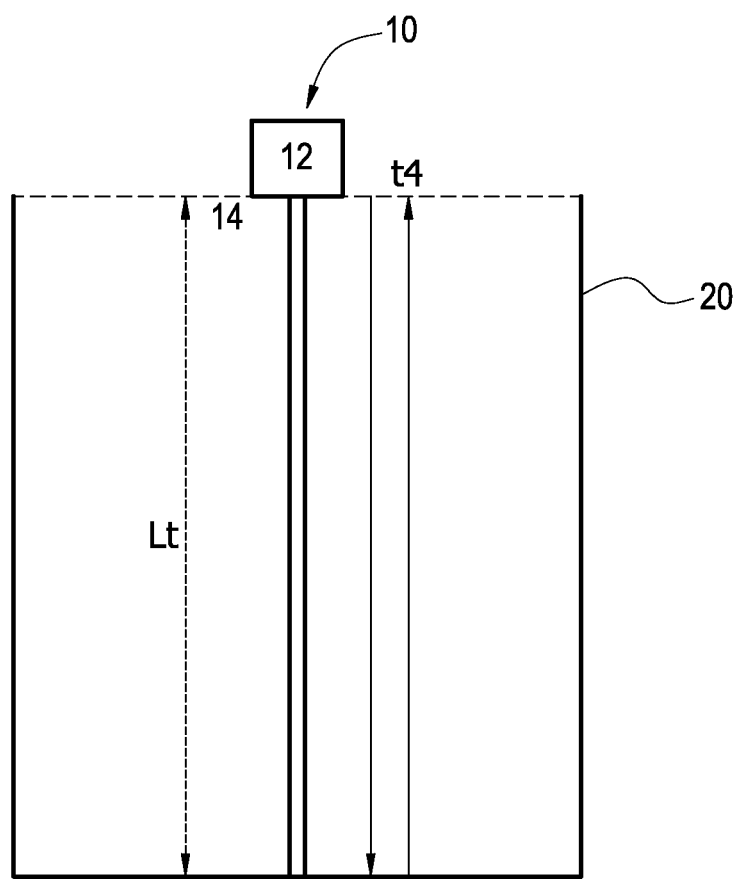
FIG. 4b shows another part of the method for measuring the depth of the material.

FIG. 4a shows a part of the method for measuring the depth of the material. FIG. 4b shows another part of the method for measuring the depth of the material. An Lm indicates the depth (namely, the level) of the material 30. An Lt indicates a sensing rod length of the sensing rod 14 (namely, a depth of the tank 20). A t3 indicates a third time-passing difference value. A t4 indicates a fourth time-passing difference value. Therefore, following equations are obtained.

$$t3=[2*(Lt-Lm)/Vair]+(2*Lm/Vm)$$

$$t4=2*Lt/Vair$$

$$Vair=c$$

$$Vm=c/\sqrt{\varepsilon}$$

$$t3-t4=(-2*Lm/c)+[2*Lm/c\sqrt{\varepsilon})]=(-2*Lm/c)+(2*Lm*\sqrt{\varepsilon}/c)=2*Lm*(\sqrt{\varepsilon}-1)/c$$

The third time-passing difference value t3, the fourth time-passing difference value t4, the permittivity ε and the constant c are known, so the depth Lm of the material 30 is obtained according to the equations mentioned above.

Moreover, in order to increase the usability of the material level sensor 10, the material level sensor 10 further comprises a time-expanding circuit (not shown in FIG. 2a, FIG. 2b, FIG. 4a or FIG. 4b, and arranged in the material level sensing circuit 12). The time-expanding circuit multiplies the feature value variation mentioned above (namely, t1-t2, or t3-t4) by a gain value, so that a unit of the feature value variation is multiplied from a microsecond to a millisecond. Therefore, the usability of the material level sensor 10 is increased.

The advantage of the present invention is to measure and calculate the permittivity ε of the material 30 to improve the accuracy of the material level sensor 10.

Although the present invention has been described with reference to the preferred embodiment thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A method for measuring a permittivity (ε) of a material (30), the method applied to a material level sensor (10), a tank (20) and the material (30), the material level sensor (10) comprising a material level sensing circuit (12) and a sensing rod (14), a top-down of the tank (20) comprising a non-filled area (22) and a filled area (24) filled with the material (30), the method comprising:

a. the sensing rod (14) of the material level sensor (10) inserting into the tank (20), so that a part of the sensing rod (14) of the material level sensor (10) is in the non-filled area (22) of the tank (20), and the other part of the sensing rod (14) of the material level sensor (10) is in the filled area (24) of the tank (20), and the material level sensor (10) is at a first location;

b. after the material level sensor (10) is at the first location, the material level sensor (10) proceeding with a material level measurement of the material (30) to obtain a first feature value;

c. after the first feature value is obtained, the material level sensor (10) being vertically moved with a vertical distance (Hair), but the sensing rod (14) of the material level sensor (10) being not completely away from the filled area (24) of the tank (20), and the material level sensor (10) being at a second location, wherein the vertical distance (Hair) is greater than zero;

d. after the material level sensor (10) is at the second location, the material level sensor (10) proceeding with the material level measurement of the material (30) to obtain a second feature value;

e. the material level sensing circuit (12) subtracting the first feature value by the second feature value to obtain a feature value variation; and f. the material level sensing circuit (12) calculating the feature value variation to obtain the permittivity (ε) of the material (30).

2. The method in claim 1, wherein the material level sensor (10) is a time domain reflection radar sensor.

3. The method in claim 2, wherein the first feature value is a first time-passing difference value (t1).

4. The method in claim 3, wherein the second feature value is a second time-passing difference value (t2).

5. The method in claim 4, wherein when the material level sensor (10) is at the first location, a length of the part of the sensing rod (14) of the material level sensor (10) in the non-filled area (22) of the tank (20) is a first length (dair), and a length of the other part of the sensing rod (14) of the material level sensor (10) in the filled area (24) of the tank (20) is a second length (dm).

6. The method in claim 5, wherein the first time-passing difference value (t1) is equal to a first time (t01) added by a second time (t02); the first time (t01) is equal to double the first length (dair) divided by an air-wave velocity (Vair); the second time (t02) is equal to double the second length (dm) divided by a material-wave velocity (Vm).

7. The method in claim 6, wherein a third length (d3) is equal to the first length (dair) added by the vertical distance (Hair); a fourth length (d4) is equal to the second length (dm) subtracted by the vertical distance (Hm).

8. The method in claim 7, wherein the second time-passing difference value (t2) is equal to a third time (t03) added by a fourth time (t04); the third time (t03) is equal to double the third length (d3) divided by the air-wave velocity (Vair); the fourth time (t04) is equal to double the fourth length (d4) divided by the material-wave velocity (Vm).

9. The method in claim 8, wherein the air-wave velocity (Vair) is a constant (c); a square root of the permittivity (ε) is a square root value ($\sqrt{\varepsilon}$); the material-wave velocity (Vm) is equal to the constant (c) divided by the square root value ($\sqrt{\varepsilon}$).

10. The method in claim 9, wherein the material level sensor (10) further comprises a time-expanding circuit; the time-expanding circuit multiplies the feature value variation by a gain value, so that a unit of the feature value variation is multiplied from a microsecond to a millisecond.

* * * * *